United States Patent [19]

White et al.

[11] Patent Number: 4,855,483

[45] Date of Patent: Aug. 8, 1989

[54] METHOD FOR PREPARING POLYSALICYLATES

[75] Inventors: Dwain M. White, Schenectady; Laura A. Socha, Troy, both of N.Y.

[73] Assignee: General Electric Company, Schenectady, N.Y.

[21] Appl. No.: 157,010

[22] Filed: Feb. 18, 1988

[51] Int. Cl.$^4$ .............................................. C07C 69/76
[52] U.S. Cl. ...................................................... 560/66
[58] Field of Search ........................................... 560/66

[56] References Cited

FOREIGN PATENT DOCUMENTS 4121610 12/1966 Japan ..................................... 560/66

OTHER PUBLICATIONS

Dean et al., *J.C.S. Perkin I*, "Synthesis of cis-Disalicylide and of Flavones Containing a Chromeno [4,3-b]-chromen Nucleus", pp. 2007–2010.
Baker et al., *J. Chem. Soc.*, 1951, 201, "Eight- and Higher-membered Ring Compounds. Part II. Di-, Tri-, Tetra-, and Hexa-salicylides", pp. 201–208.
Saegusa et al., *Polymer Bulletin* 1,(1979), "Polymerization of Anhydro-Q-carboxysalicylic Acid", pp. 341–345.
Ogata et al., *Synthetic High Polymers*, vol. 81 (1974), "Synthesis of Polymers from m-Hydroxybenzoic Acid. 4'. Synthesis of Various Polymers From m-hydroxybenzoic Acid", p. 3 (Abstract from *Chemical Abstracts*).

*Primary Examiner*—Bruce Gray
*Attorney, Agent, or Firm*—Mary Ann Montebello; James C. Davis, Jr.; William H. Pittman

[57] ABSTRACT

Polysalicylates are prepared according to the present invention by the reaction of salicylic acid with a carboxylic acid derivative such as acetic anhydride or acetyl chloride. The reaction is carried out under conditions which yield greater than about 90% by weight linear polysalicylate product.

13 Claims, No Drawings

METHOD FOR PREPARING POLYSALICYLATES

This invention relates generally to polysalicylates, and more particularly to an improved method for the preparation thereof.

The formation of certain polymers often involves the generation of reactive end groups. Examples of these types of polymers are the polyphenylene ethers, a well-known class of polymers characterized by excellent chemical, physical and electrical properties. When polyphenylene ethers are formed by oxidative coupling reactions, terminal hydroxy groups are formed on the polyphenylene ether chain. It is believed that the oxidation of such groups results in the tendency of polyphenylene ethers to become dark-colored and brittle when exposed to extreme conditions such as high temperature, particularly in the presence of oxygen.

One method for inactivating the hydroxy groups and thereby overcoming these disadvantages involves capping the groups, e.g., by acylation.

Very effective capping agents for polyphenylene ethers and other polymers such as polyetherimides are the polysalicylates. One advantage of some of the polysalicylate capping agents is the fact that their use does not result in the large scale formation of undesirable by-products of the capping reaction, such as chloride compounds.

Polysalicylates have been prepared by several methods. For example, Saegusa et al. discloses such preparation by the anionic polymerization of salicylic carbonate. *Polymer Bulletin* 1, 341-345 (1979). Furthermore, polysalicylates have been found to be the main product (rather than the reported disalicylide) of a process taught by Dean et al., which involves the treatment of salicylic carbonate with a catalytic amount of triethylamine. *J. Chem. Soc.*, Perkin I, 1972, 2007-2010.

A need exists—especially in a commercial environment—for a simple, economical method of preparing polysalicylates in high yield. It is therefore a primary object of the present invention to provide an improved process for preparing polysalicylates.

Another object of the present invention is to provide a method for the high-yield preparation of polysalicylates from inexpensive starting materials.

SUMMARY OF THE INVENTION

The aforementioned objects are achieved by a method for preparing polysalicylates which comprises reaction of salicylic acid with a carboxylic acid derivative having the formula

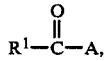

wherein
A is a halogen or

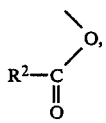

and
$R^1$ and $R^2$ are individually hydrogen or straight or branched alkyl groups containing from about 1 to about 5 carbon atoms. The preferred carboxylic acid derivative is acetic anhydride. Furthermore, the reaction is carried out at a temperature low enough to yield greater than about 90% by weight linear polysalicylate product and less than about 10% by weight cyclic salicylide product.

DETAILED DESCRIPTION OF THE INVENTION

According to the present invention, salicylic acid is reacted with a carboxylic acid derivative having the formula described above. $R^1$ and $R^2$ may each be hydrogen or an alkyl group containing from about 1 to 5 carbon atoms. Suitable alkyl groups include methyl, ethyl, propyl, isopropyl, butyl, and pentyl. These alkyl groups may be substituted with various substituents, such as chlorine, fluorine, or iodine. In preferred embodiments, $R^1$ and $R^2$ are either unsubstituted methyl or ethyl groups, since the lower boiling points which these compounds generally exhibit result in more convenient distillation of the reaction mixture. Methyl groups are most preferred.

Exemplary acid chlorides which can serve as the carboxylic acid derivative include acetyl chloride, propionyl chloride, butyryl chloride, and isobutyryl chloride. Acetyl chloride is the preferred acid chloride when viewed in terms of cost and practicality.

Exemplary acid anhydrides which can serve as the carboxylic acid derivative include acetic anhydride, propionyl anhydride, trifluoroacetic acid anhydride, butyric anhydride, and isobutyric anhydride.

The acid anhydrides are the preferred carboxylic acid derivatives for this process because their reaction with salicylic acid does not result in undesirable by-products which might remain in the polysalicylate product. In terms of availability, cost, and effectiveness, acetic anhydride is the most preferred acid anhydride.

Equimolar amounts of salicylic acid and the carboxylic acid derivative are usually used. If greater amounts of the carboxylic acid derivative are employed, the excess is simply distilled away; whereas greater amounts of salicylic acid employed may result in a lower molecular weight polysalicylate product. In terms of efficiency on a commercial scale, the molar ratio of salicylic acid to the carboxylic acid derivative may range from about 1.0:0.8 to about 1.0:2.0.

The salicylic acid and the carboxylic acid derivative are reacted at a temperature low enough to yield a maximum of polysalicylate product, i.e., to substantially prevent the formation of cyclic salicylate products such as di- and trisalicylides, while also preventing the formation of other by-products which form at even higher temperatures, such as xanthone. Thus, the temperature maintained is one which results in the production of less than 10% by weight, and preferably less than 5% by weight, cyclic salicylate product, as measured by gel permeation chromatography (GPC) techniques. Reaction temperatures in the range of about 140° C. to about 280° C. are generally suitable, with temperatures in the range of about 220° C.-250° C. being most preferred.

The duration of the reaction is dependent on various factors, such as the particular carboxylic acid derivative employed and the reactor size. For example, although 1 to 4 hours is generally sufficient for complete reaction, large scale mixtures such as those in the 100 gallon range may require up to about 10 hours to absorb enough heat for complete reaction.

In some embodiments of the present invention, the reaction mixture is heated gradually within either of the temperature ranges described above. For example, a reaction mixture containing salicylic acid and acetic anhydride could be raised to a temperature of about 140° C., and then gradually heated over the course of about 60 minutes to 220° C. This type of heating schedule permits the acetic acid to be distilled from the reaction mixture in a more uniform manner.

Volatile by-products are removed from the mixture throughout reaction by well-known techniques, such as vacuum distillation. When the carboxylic acid derivative is acetic anhydride, the volatile by-products mainly comprise acetic acid.

The liquid polysalicylate product is usually solidified to a glass-like material upon cooling. If desired, the glass may be ground to a powder for further use or storage.

The polysalicylate product prepared by the method of the present invention usually contains about 1 acetate end group for every 15-50 salicylate repeat units. The smaller proportions of acetate end groups can be achieved when higher reaction temperatures and longer heating times within the above ranges are used.

The isolated yield of polysalicylate from this process is at least about 90%, based on the amount of salicylic acid employed.

The molecular weight (number average) for the polysalicylate product usually ranges from about 500 to about 1500.

It is clear from the foregoing that the process of this invention is a high-yield, one-step synthesis of linear polysalicylates from inexpensive starting materials. The product is prepared at a lower cost than cyclic salicylate materials, but is just as effective a capping agent. The polysalicylates are of great use as capping agents for polyphenylene ethers, as described in U.S. Pat. No. 4,760,118 and incorporated herein by reference. In comparison to uncapped polyphenylene ethers, the capped polyphenylene ethers are much less susceptible to oxidative degradation at high temperatures. Furthermore, capping by the use of materials made by this process may be efficiently conducted in the melt during polymer extrusion or similar operations, thereby enhancing typical commercial processes for polyphenylene ether production. For example, since linear polysalicylates are quite fluid at about 200° C., they are more amenable to extruder applications than many of the cyclic polysalicylates which have melting points above 200° C.

The following examples illustrate embodiments of the present invention. All proportions and percentages disclosed herein are by weight, unless otherwise indicated.

The GPC measurements were made on a Waters liquid chromatograph with μ-styragel columns (500, 500, 100, 100 Angstroms) and chloroform (with 0.5% ethanol), using a calibration with linear polysalicylate oligomers unless otherwise stated.

The nuclear magnetic resonance devices used were a Varian XL 300 spectrometer for $^{13}$C-NMR spectra, and a Varian EM 390 spectrometer for $^1$H-NMR spectra.

EXAMPLE 1

This example describes the preparation of polysalicylate from salicylic acid and acetic anhydride. Salicylic acid (27.6 g, 0.2 mole) and acetic anhydride (19.8 ml, 21.4 g, 0.21 mole) in a 250 ml RB flask were heated under a nitrogen atmosphere and stirred with a magnetic stirring bar. An oil bath was used for heating. The temperature of the reaction mixture was raised from 25° C. to 140° C. over the course of 2 hours as a clear solution formed. At this time, a Claisen distillation head was attached to the reaction vessel, and a vacuum (about 20 mm mercury) was applied. The temperature was raised over 1 hour to 220° C. During this period, acetic acid distilled from the mixture. As the temperature approached 220° C., a sublimate collected in the upper part of the apparatus. This material, having a weight of 2.7 g, was determined to be a mixture of salicylic acid (1.6 g), aspirin (0.9 g), and acetic acid (0.2 g). A vacuum pump was attached for about 15 minutes to remove the remaining acetic acid. The pot residue was then cooled to form a solid glass which was ground up in a mortar and pestle. The weight of the material was 22.3 g.

Analysis by $^1$H-NMR confirmed that the product was linear polysalicylic acid. It consisted mainly of salicylate repeat units, with about 1 acetate end group for every 15 salicylate repeat units. The number average molecular weight as determined by GPC was 865.

EXAMPLE 2

This example describes the large scale production of polysalicylates. A 50 gallon glass-lined Pfaudler reactor was equipped with a retreating curve impeller, thermocouple probe, vacuum/pressure gauge, and distilling condenser with a nitrogen bypass. In addition, the distilling condenser was equipped with a double vacuum receiver which was chilled with ice to collect the acetic acid distillate. The reactor was charged with 60.4 kg of salicylic acid (437.3 moles) and 46.0 kg of acetic anhydride (450.9 moles). The resulting slurry was heated slowly to a reflux temperature of about 143° C. The nitrogen gas was turned off, and a light vacuum was applied. Adjustments were made to control acetic acid evolution. After approximately 5 liters of acetic acid had been removed, the pressure was reduced to 250 mm mercury. The temperature and vacuum were increased slowly over a 2 hour period to a maximum of 242° C. and 11 mm mercury, respectively. This temperature/pressure regimen was maintained for about 1 hour after the last appearance of liquid distillate. The heat and vacuum were turned off, and a sample was removed.

$^1$H-NMR analysis indicated a polysalicylate/acetate molar ratio of about 20:1. The heat and vacuum were resumed for about 1 hour. A heating tape was applied to the bottom drain valve of the reaction vessel, and turned up to a temperature of about 225° C. The vacuum was then turned off, and the reactor contents were drained into a large stainless steel drum, providing a yield of about 105 lbs of polysalicylate, which represented 70.9% by weight, based on the amount of salicylic acid employed. The glass-like solid which formed in the steel drum upon cooling was physically broken up and granulated, using a large Henschel mixer. The weight average molecular weight of the material as measured by GPC was 2465. This material was subsequently employed to cap polyphenylene ether polymer in the melt during an extrusion operation.

Modifications and variations of the present invention are possible in light of the above teachings. It should therefore be understood that changes may be made in particular embodiments herein which are within the full intended scope of the invention as defined by the appended claims.

What is claimed is:

1. A method for preparing linear polysalicylates, comprising the reaction of salicylic acid with a carboxylic acid derivative having the formula

wherein A is a halogen or

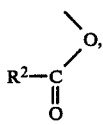

and $R^1$ and $R^2$ are individually hydrogen or straight or branched alkyl groups containing from about 1 to about 5 carbon atoms, at a temperature ranging from about 140° C. to about 280° C.

2. The method of claim 1 wherein the carboxylic acid derivative is acetyl chloride.

3. The method of claim 1 wherein the carboxylic acid derivative is selected from the group consisting of acetic anhydride, propionyl anhydride, trifluoroacetic acid anhydride, butyric anhydride, and isobutyric anhydride.

4. The method of claim 1 wherein $R^1$ and $R^2$ are individually selected from the group consisting of methyl and ethyl groups.

5. The method of claim 4 wherein the carboxylic acid derivative is acetic anhydride.

6. The method of claim 1 wherein the molar ratio of salicylic acid to carboxylic acid derivative is about 1.0:0.8 to about 1.0:2.0.

7. The method of claim 6 wherein the molar ratio is about 1:1.

8. The method of claim 6 wherein the salicylic acid and the carboxylic acid derivative are reacted at a temperature low enough to yield greater than about 90% by weight linear product and less than about 10% by weight cyclic product.

9. The method of claim 8 wherein the reaction is carried out for about 1 to 10 hours.

10. The method of claim 8 wherein volatile by-products are vacuum-distilled from the product during the reaction.

11. The method of claim 10 wherein the carboxylic acid derivative is acetic anhydride, and the volatile by-products comprise acetic acid.

12. The method of claim 8 wherein the reaction temperature is maintained in the range of about 220° C. to about 250° C.

13. The method of claim 12 wherein the carboxylic acid derivative is acetic anhydride.

* * * * *